US00PP32510P2

(12) United States Plant Patent
Schroll

(10) Patent No.: US PP32,510 P2
(45) Date of Patent: Nov. 24, 2020

(54) ***HYDRANGEA* PLANT NAMED 'SCHROLL122-11-01A'**

(50) Latin Name: *Hydrangea macrophylla*
Varietal Denomination: SCHROLL122-11-01a

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 16/873,045

(22) Filed: Jan. 21, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'SCHROLL122-11-01a', characterized by its compact, upright and mounded plant habit; moderately vigorous growth habit; freely branching habit and strong stems; dark green-colored leaves; mophead-type inflorescences with light red purple-colored sterile flowers; when "blued", that is, treated with aluminum sulfate, sterile flowers are violet blue in color; long flowering period; and good postproduction quality and longevity.

3 Drawing Sheets

Figure 1:
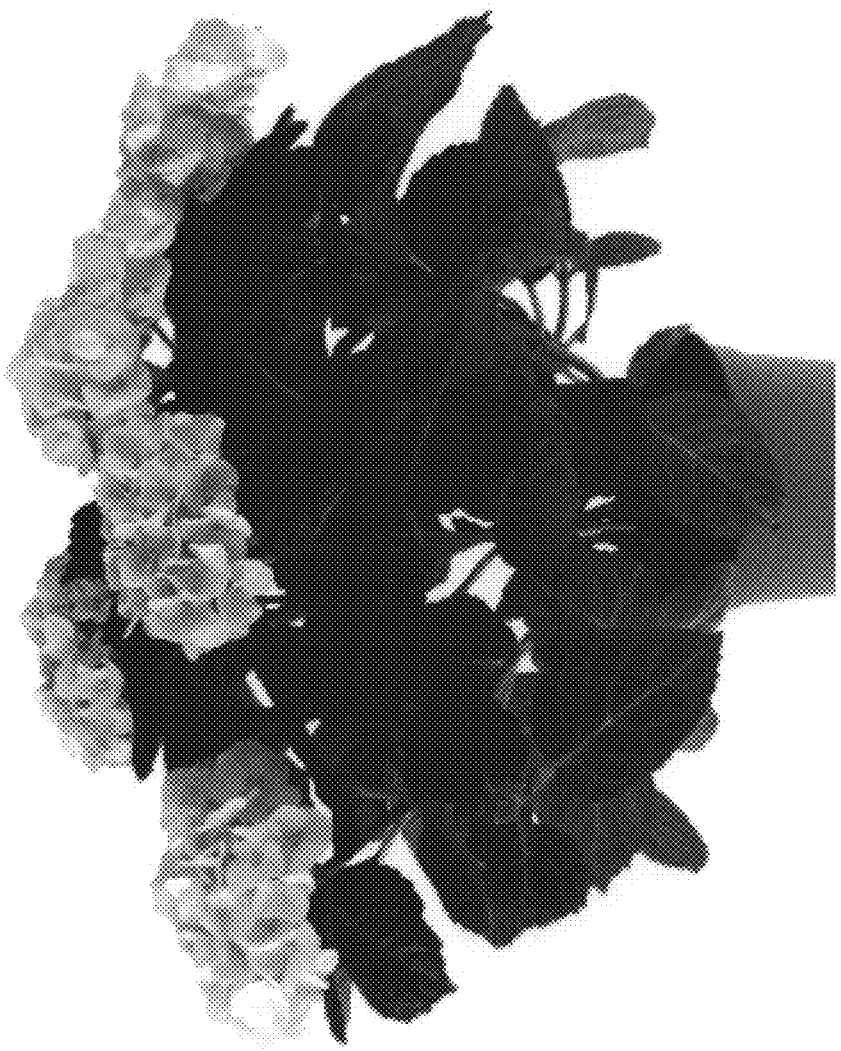

Botanical designation: *Hydrangea macrophylla.*
Cultivar denomination: 'SCHROLL122-11-01a'.

BACKGROUND OF THE INVENTION

The present invention relates to a new and distinct cultivar of *Hydrangea* plant, botanically known as *Hydrangea macrophylla* and hereinafter referred to by the name 'SCHROLL122-11-01a'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2011 of a proprietary selection of *Hydrangea macrophylla* identified as code designation Schroll080108, not patented, as the female, or seed, parent with a proprietary selection of *Hydrangea macrophylla* identified as code number 32-00, not patented, as the male, or pollen, parent. The new *Hydrangea* plant was discovered and selected by the Inventor during the spring of 2013 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2013 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL122-11-01a'. These characteristics in combination distinguish 'SCHROLL122-11-01a' as a new and distinct *Hydrangea* plant:

1. Compact, upright and mounded plant habit.
2. Moderately vigorous growth habit.
3. Freely branching habit and strong stems.
4. Dark green-colored leaves.
5. Mophead-type inflorescences with light red purple-colored sterile flowers; when "blued", that is, treated with aluminum sulfate, sterile flowers are violet blue in color.
6. Long flowering period.
7. Good postproduction quality and longevity.

Plants of the new *Hydrangea* differ primarily from plants of the female selection parent in the following characteristics:

1. Plants of the new *Hydrangea* are more compact than and not as vigorous as plants of the female parent selection.
2. Plants of the new *Hydrangea* are more freely branching than plants of the female parent selection.
3. Inflorescences of plants of the new *Hydrangea* are smaller than inflorescences of plants of the female parent selection.
4. Plants of the new *Hydrangea* and the female parent selection differ in sterile flower color as sterile flowers of plants of the new *Hydrangea* are darker in color than plants of the female parent selection.

Plants of the new *Hydrangea* differ primarily from plants of the male selection parent in the following characteristics:

1. Plants of the new *Hydrangea* are more compact than and not as vigorous as plants of the male parent selection.
2. Plants of the new *Hydrangea* are more freely branching and have stronger lateral branches than plants of the male parent selection.
3. Plants of the new *Hydrangea* and the male parent selection differ in sterile flower color as sterile flowers of plants of the new *Hydrangea* are lighter in color than plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Plants of the new *Hydrangea* are more freely branching than plants of 'H213901'.
3. Inflorescences of plants of the new *Hydrangea* are smaller than inflorescences of plants of 'H213901'.
4. Sepals of sterile flowers of the new *Hydrangea* are not as undulate as sepals of sterile flowers of 'H213901'.
5. Plants of the new *Hydrangea* and 'H213901' differ in sterile flower color as sterile flowers of plants of the new *Hydrangea* are lighter in color than sterile flowers of plants of 'H213901'.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are stronger and more sturdy than plants of 'H213906'.
2. Plants of the new *Hydrangea* are more freely branching than plants of 'H213906'.
3. Plants of the new *Hydrangea* force slightly faster than plants of 'H213906'.
4. Plants of the new *Hydrangea* and 'H213906' differ in sterile flower color as sterile flowers of plants of the new *Hydrangea* are lighter in color than sterile flowers of plants of 'H213906'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 3) comprises a side perspective view of a typical flowering plant of 'SCHROLL122-11-01a' grown in a container that has not been "blued".

Figure 2:
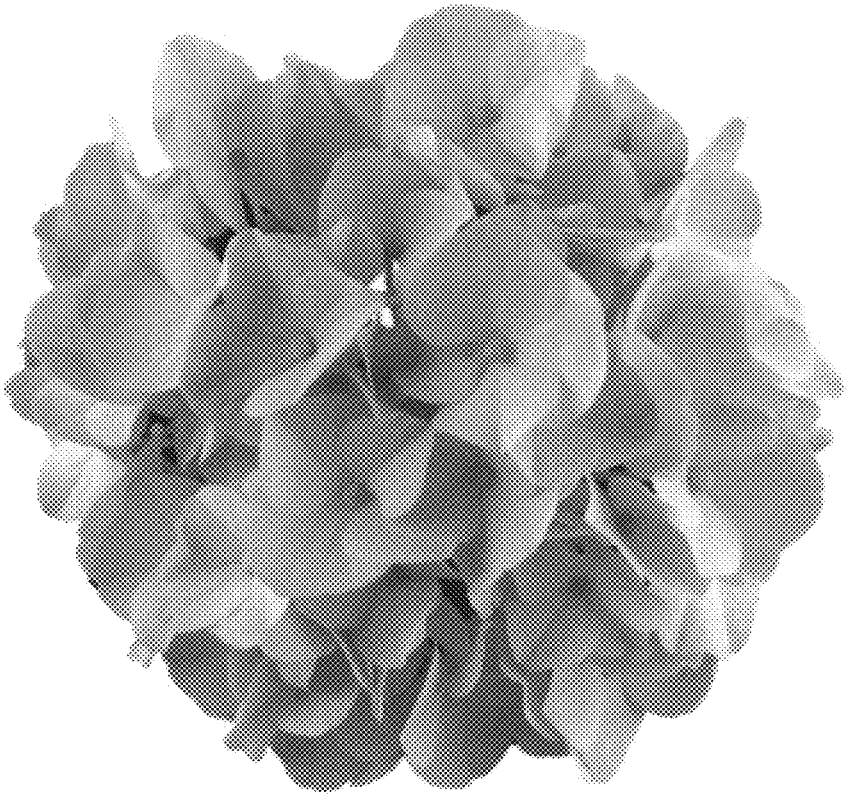

The photograph on the second sheet (FIG. 2 of 3) is a close-up view of a typical inflorescence of 'SCHROLL122-11-01a' that has not been "blued".

Figure 3:
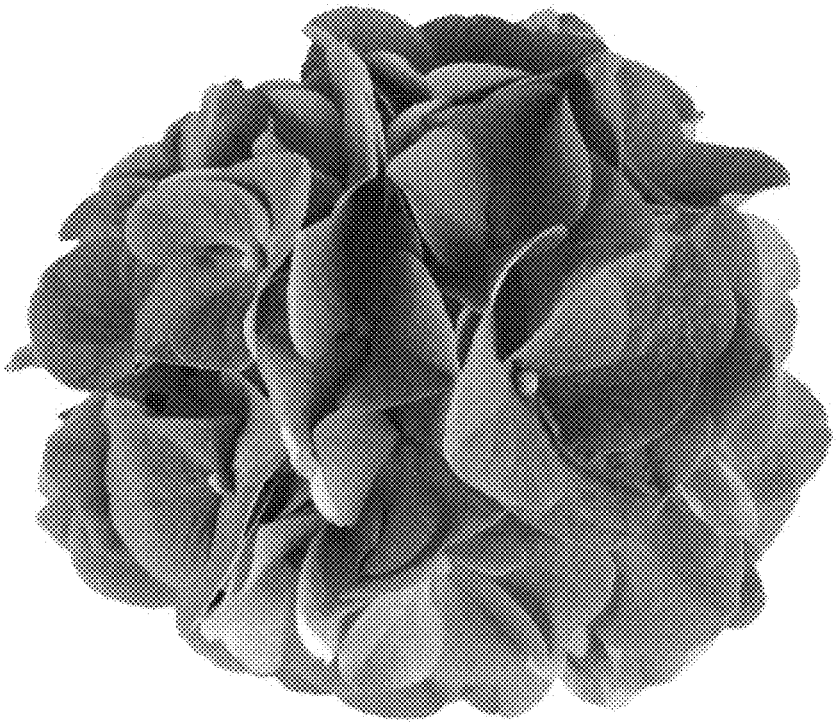

The photograph on the third sheet (FIG. 3 of 3) is a close-up view of a typical inflorescence of 'SCHROLL122-11-01a' that has been "blued".

DETAILED BOTANICAL DESCRIPTION

Plants used in the aforementioned photographs and in the following description were grown during the late winter in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL122-11-01a'.

Parentage:

*Female, or seed, parent*.—Proprietary selection of *Hydrangea macrophylla* identified as code designation Schroll080108, not patented.

*Male, or pollen, parent*.—Proprietary selection of *Hydrangea macrophylla* identified as code number 32-00, not patented.

Propagation:

*Type cutting*.—By softwood cuttings.

*Time to initiate roots, summer*.—About 14 to 15 days at temperatures about 20° C.

*Time to initiate roots, winter*.—About 20 days at temperatures about 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Freely branching; medium density.

Plant description:

*Plant and growth habit*.—Perennial subshrub; compact, upright and mounded plant habit; broadly inverted triangle; freely branching habit with about six to eight lateral branches developing per plant; strong lateral branches; moderately vigorous growth habit.

*Plant height*.—About 25 cm.

*Plant diameter or area of spread*.—About 35 cm.

*Lateral branches*.—Length: About 9 cm to 12 cm. Diameter: About 4 mm to 6 mm. Internode length: About 3 cm to 5 cm. Strength: Strong, sturdy. Texture: Smooth, glabrous. Color, developing and developed: Close to 144A. Color, lenticels: Close to N199B.

Leaf description:

*Arrangement*.—Opposite, decussate; simple.

*Length*.—About 8 cm to 10 cm.

*Width*.—About 5.5 cm to 6.5 cm.

*Shape*.—Ovate.

*Apex*.—Acute to cuspidate.

*Base*.—Obtuse.

*Margin*.—Serrate.

*Texture, upper surface*.—Smooth to rugose, glabrous.

*Texture, lower surface*.—Rugose, glabrous.

*Venation pattern*.—Pinnate, reticulate.

*Color*.—Developing leaves, upper surface: Close to 137A. Developing leaves, lower surface: Close to 137C. Fully expanded leaves, upper surface: Close to 137A; venation, close to 145C to 145D. Fully expanded leaves, lower surface: Close to 137D; venation, close to 145C to 145D.

*Petioles*.—Length: About 2 cm to 3 cm. Diameter: About 3 mm to 4 mm. Strength: Strong. Texture, upper and lower surfaces: Smooth, glabrous. Color, upper surface: Close to 144A. Color, lower surface: Close to 144B.

Inflorescence & flower description:

*Flower type and habit*.—Showy single sterile and inconspicuous single fertile flowers arranged on terminal mophead-type panicles; panicles globular to almost spherical in overall shape; fertile flowers face upright to outwardly and sterile flowers face mostly upright to outwardly depending on their position on the inflorescence; early flowering habit, plants begin flowering about eight to ten weeks after forcing period.

*Natural flowering season*.—Long flowering period, continuous flowering from the late summer (July/August) until frost in Northern Europe.

*Flower longevity, fertile flowers*.—Flowers last about one month on the plant; fertile flowers not persistent.

*Flower longevity, sterile flowers*.—Flowers last about two months on the plant; sterile flowers persistent.

*Quantity of flowers*.—Freely flowering habit with about 50 fertile flowers and about 60 sterile flowers per panicle.

*Fragrance*.—None detected.

*Panicle height*.—About 6 cm to 7 cm.

*Panicle diameter*.—About 12 cm to 15 cm.

*Flower diameter, fertile flowers*.—About 3 mm to 4 mm.

*Flower depth* (*height*), *fertile flowers*.—About 2 mm to 3 mm.

*Flower diameter, sterile flowers*.—About 5 cm.

*Flower depth* (*height*), *sterile flowers*.—About 1.5 cm.

*Flower shape, fertile flowers*.—Spherical.

*Flower shape, sterile flowers*.—Rounded.

*Flower buds, fertile flowers*.—Length: About 3 mm. Diameter: About 3 mm. Shape: Spherical. Color: Close to 36D.

*Flower buds, sterile flowers*.—Length: About 3 mm. Diameter: About 3 mm. Shape: Spherical. Color: Close to 2C.

*Petals, fertile flowers*.—To date, petal development on fertile flowers has not been observed on plants of the new *Hydrangea*.

*Petals, sterile flowers*.—Quantity and arrangement: Four in a single whorl. Length: About 3.2 mm. Width: About 2 mm. Shape: Elliptic. Apex: Rounded. Base: Rounded to truncate. Margin: Entire. Texture, upper and lower surfaces: Smooth, glabrous. Color: When opening, upper and lower surfaces: Close to 62D; when "blued", close to 62D. Fully opened, upper and lower surfaces: Close to 155D; when "blued", close to 155D; color does not change with development.

*Sepals, fertile flowers*.—Quantity and arrangement: About five in a single whorl. Length: About 2 mm to 3 mm. Width: About 1 mm to 2 mm. Shape: Deltoid. Apex: Acute. Base: Cuneate. Margin: Entire. Texture, upper and lower surfaces: Smooth, glabrous. Color: When opening, upper and lower surfaces: Close to NN155B; when "blued", close to 145D. Fully opened, upper and lower surfaces: Close to NN155B; when "blued", close to 145D; color becoming closer to 62C with development.

*Sepals, sterile flowers*.—Quantity and arrangement: Four in a single whorl. Length: About 2.5 cm. Width: About 3.5 cm. Shape: Deltoid to ovate. Apex: Retuse. Base: Broadly cuneate. Margin: Entire. Texture, upper and lower surfaces: Smooth, glabrous. Color, plants not "blued": When opening, upper and lower surfaces: Initially, close to 145C becoming closer to 155B with development; towards the apex, close to N66D. Fully opened, upper and lower surfaces: Close to N66D; color does not change with development. Color, plants "blued": When opening, upper surface: Close to 68B. When opening, lower surface: Close to 155A. Fully opened, upper surface: Close to 94B; towards the base, close to N81B. Fully opened, lower surface: Close to 94B.

*Pedicels, fertile flowers*.—Length: About 1 cm to 1.5 cm. Diameter: About 1 mm. Strength: Strong. Aspect: Mostly upright. Texture: Smooth, glabrous. Color: Close to 63C.

*Pedicels, sterile flowers*.—Length: About 2.5 cm. Diameter: About 1.5 mm. Strength: Strong. Aspect: About 10° to 90° from vertical depending on position in the panicle. Texture: Pubescent. Color, plants not "blued": Close to 157B. Color, plants "blued": Close to 150C.

*Reproductive organs, fertile flowers*.—Stamens: Quantity per flower: About eight. Filament length: About 3 mm to 4 mm. Filament color: Close to NN155B. Anther length: About 1 mm. Anther shape: Ovate. Anther color: Close to NN155B. Pollen amount: Abundant. Pollen color: Close to NN155B. Pistils: Pistil quantity per flower: About three or four. Pistil length: Less than 1 mm. Stigma shape: Oval. Stigma color: Close to NN155B. Style length: Less than 1 mm. Style color: Close to NN155B. Ovary color: Close to NN155B.

*Reproductive organs, sterile flowers*.—Stamens: Quantity per flower: About eight to ten. Filament length: About 2 mm to 3 mm. Filament color: Close to 155D. Anther length: About 1 mm. Anther shape: Ovate. Anther color: Close to 155D. Pollen amount: Scarce. Pollen color: Close to 150D. Pistils: Pistil quantity per flower: If present, about three. Pistil length: About 1 mm to 2 mm. Stigma shape: Three-lobed. Stigma color: Close to 157C. Style length: About 1 mm to 2 mm. Style color: Close to 157C. Ovary color: Close to N144C.

*Seeds*.—To date, seed development has not been observed on plants of the new *Hydrangea*.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to 38° C.

It is claimed:

1. A new and distinct *Hydrangea* plant named 'SCHROLL122-11-01a' as illustrated and described.

* * * * *